United States Patent
Ma et al.

(10) Patent No.: US 8,603,776 B2
(45) Date of Patent: Dec. 10, 2013

(54) METHOD FOR PREPARING XYLOSE-UTILIZING STRAIN

(75) Inventors: Tien-Yang Ma, Longtan Township (TW); Ting-Hsiang Lin, Longtan Township (TW); Teng-Chieh Hsu, Taitung (TW); Chiung-Fang Huang, Longtan Township (TW); Gia-Leun Guo, New Taipei (TW); Wen-Song Hwang, Longtan Township (TW); Jia-Baau Wang, Taipei (TW); Yun-Peng Chao, Taichung (TW); Guan-Lin Yeh, Longtan Township (TW)

(73) Assignee: Institute of Nuclear Energy Research Atomic Energy Council, Executive Yuan, Longtan Township, Taoyuan County (TW)

( * ) Notice: Subject to any disclaimer, the term of this patent is extended or adjusted under 35 U.S.C. 154(b) by 113 days.

(21) Appl. No.: 13/242,547

(22) Filed: Sep. 23, 2011

(65) Prior Publication Data
US 2012/0309093 A1    Dec. 6, 2012

(30) Foreign Application Priority Data
Jun. 3, 2011    (TW) .................................. 100119583

(51) Int. Cl.
*C12P 21/06*    (2006.01)

(52) U.S. Cl.
USPC .. 435/69.1; 435/69.7; 435/320.1; 435/254.21

(58) Field of Classification Search
None
See application file for complete search history.

(56) References Cited

U.S. PATENT DOCUMENTS

| | | | |
|---|---|---|---|
| 5,789,210 A * | 8/1998 | Ho et al. ........................ | 435/163 |
| 6,333,181 B1 * | 12/2001 | Ingram et al. ................. | 435/165 |
| 7,226,735 B2 * | 6/2007 | Jeffries et al. ................ | 435/6.18 |
| 7,527,927 B1 * | 5/2009 | Ho et al. ....................... | 435/6.18 |
| 2003/0235881 A1 * | 12/2003 | Heikkila et al. ............. | 435/69.1 |

FOREIGN PATENT DOCUMENTS

WO    WO 91/15588    * 10/1991

* cited by examiner

*Primary Examiner* — Jennifer Graser
(74) *Attorney, Agent, or Firm* — Hoffmann & Baron, LLP (57) ABSTRACT

A method for preparing a xylose-utilizing strain of *Saccharomyces cerevisiae* and the *Saccharomyces cerevisiae* are introduced. The preferred recombinant strain contains multiple copies of integrated xylose metabolic genes, and can rapidly ferment xylose to produce ethanol from synthetic medium and lignocellulosic raw materials. The xylose-utilizing strain is applicable for the cellulosic ethanol production industry and brewing industry.

4 Claims, 5 Drawing Sheets

METHOD FOR PREPARING XYLOSE-UTILIZING STRAIN

CROSS-REFERENCE TO RELATED APPLICATION

This non-provisional application claims priority under 35 U.S.C. §119(a) on Patent Application No(s). 100119583 filed in Taiwan, R.O.C. on Jun. 3, 2011, the entire contents of which are hereby incorporated by reference.

FIELD OF INVENTION

The present invention relates to a method for preparing a xylose-utilizing *Saccharomyces cerevisiae*. The preferred recombinant strain contains multiple copies of integrated xylose metabolic genes encoding xylose reductase, xylose dehydrogenase, xylulokinase and transaldolase, and can rapidly ferment xylose to ethanol from synthetic medium and lignocellulosic raw materials. This xylose-utilizing strain can be potentially used for cellulosic, ethanol production and brewing industry.

BACKGROUND OF INVENTION

Bioethanol is one of the most promising alternatives to petroleum-based fuels. Lignocellulosic biomass, such as woods and agricultural residues, is an attractive feedstock for bioethanol production because of their relatively low cost, great abundance, sustainable supply and without food conflict. Lignocellulosic materials are mainly composed of cellulose, hemicellulose, and lignin. Of these, only cellulose and hemicellulose can be used to produce ethanol by fermentation of monomeric sugars obtained by saccharification including chemical or enzymatic hydrolysis. The cellulose fraction is made up of glucose, which is the most abundant sugar in lignocellulosic biomass, while 20-40% of the biomass is hemicellulose, which consists mostly of xylose. Literature often discloses using *Pichia* sp. as a strain for xylose fermentation because of its high performance in turning xylose into ethanol. However, *Pichia* sp. is intolerant to a high ethanol concentration and environmental inhibitors. Therefore, this has resulted in this strain with poor industrial application. Normally, in the pretreatment process of cellulosic raw materials, fermentation inhibitors, such as acetic acid, furfural, and hydroxymethyl furfural, each having a range of concentration levels, are produced, depending on reaction conditions. For example, 0.5~2.0 g/L of furfural reduces productivity by 29~95% and growth by 25~99%, and 1.0-5.0 g/L of hydroxymethyl furfural reduces productivity by 17~91% and growth by 5~99%. Hence, lignocellulosic hydrolysates produced in the pretreatment process is usually undergone an overliming process to remove furfural, so as to detoxify the fermentation inhibitors produced in the pretreatment process and thereby ensure the success of the hydrolysate fermentation process. However, the overliming process not only causes a loss of xylose but also contributes to the production of gypsum sludge; hence, the processing and disposal of the resultant gypsum sludge incurs costs and equipment, thereby increasing production costs.

*Saccharomyces cerevisiae* is the most attractive ethanol-producing microorganism because of its high ethanol productivity, high inhibitory compounds tolerance and safety as a GRAS organism. However, wild type *S. cerevisiae* strains rapidly ferment glucose, mannose and galactose, but not xylose. Thus, to achieve economically feasible ethanol fermentation, genetically engineered *S. cerevisiae* has been developed to improve the capacity for converting xylose into ethanol. A number of metabolic engineering strategies to enhance ethanolic xylose fermentation in *S. cerevisiae* have been explored. Several approaches have been prospected to express a xylose utilization pathway from naturally pentose-utilizing bacteria and fungi in *S. cerevisiae* either by introducing genes encoding xylose reductase (XR) and xylitol dehydrogenase (XDH), or by introducing the gene encoding xylose isomerase (XI). *Pichia stipitis*, a naturally pentose-utilizing fungus, has been chosen as the source of the heterologously expressed enzymes because of its high ethanol yield from xylose, despite only under oxygen limitation. However, the *S. cerevisiae* strains expressing the XR and XDH from *P. stipitis* produced xylitol, and the ethanol yield from xylose is low. This is attributed to the cofactor imbalance between XR and XDH. Heterologous expression of bacterial XI genes in *S. cerevisiae* has been tried for many years. However, less actively expressed XI has been reported. Despite the relatively high activity of Piromyces XI in *S. cerevisiae*, the expression of this enzyme only enables this strain to grow slowly on xylose, suggesting that the xylose metabolic flux in *S. cerevisiae* is not only affected by the conversion of xylose to xylulose.

The flux of metabolism from xylose to ethanol is affected at several levels in the pathway. The transport of xylose in *S. cerevisiae* occurs through non-specific hexose transporters, but the affinity of xylose is one to two orders of magnitude lower than hexose sugars. Therefore, xylose transport is early considered a rate-controlling step for ethanolic xylose fermentation. In addition, the production of xylitol during xylose consumption by recombinant xylose-utilizing *S. cerevisiae* is ascribed to the difference in cofactor preferences between the enzymes in the initial xylose utilization pathways. Xylitol formation in recombinant *S. cerevisiae* has been reduced by expressing mutated XR or XDH with altered cofactor affinity or to increase the NADPH pool by overexpressing the heterologous GADPH enzyme. The fact is that not only the cofactor preferences of the enzymes are involved, but also the levels of the XR and XDH activities affect xylitol formation during xylose fermentation. Increase of the XR and XDH activity, allowing an increased flux in the initial xylose pathway, significantly reduces xylitol accumulation. Increases of the XR and XDH activities have been observed in mutant *S. cerevisiae* strains with improved xylose utilization. Similarly, high activity of Piromyces XI allows higher xylose fermentation rates than the lower bacterial XI activity. The *S. cerevisiae* genome contains the gene XKS1 coding for XK, but the XK activity in wild-type *S. cerevisiae* is too low to support ethanolic xylose fermentation in strains engineered with a xylose metabolic pathway. However, it is only when additional copies of XKS1 are expressed that recombinant xylose utilizing *S. cerevisiae* produces ethanol from xylose. But, unregulated kinase activity may cause a metabolic disorder. It has experimentally been shown that only fine-tuned expression of XKS1 in *S. cerevisiae* has improved ethanol fermentation from xylose. Above all, there is not just one rate-limiting step in metabolic flux from xylose to ethanol by *S. cerevisiae* and therefore, strain engineering for enhanced capacity for xylose fermentation remains a challenge.

SUMMARY OF THE INVENTION

The present invention describes a method to enhance the ethanol yield and sugar consumption rate from xylose for recombinant *S. cerevisiae*. This goal is achieved by increasing the extra copies of xylose reductase gene to elevate the enzyme activity, and auto-tune the expression levels of the xylitol dehydrogenase and xylulokinase by dual-transforming two recombinant expression plasmids contained XDH and XK genes. This systematic method could build the *S. cerevisiae* library with different ratios of xylose metabolic genes, and well-growth colonies with different fermentation capacities of xylose could be further selected. We successfully isolated a recombinant strain with the attractive capacity for xylose fermentation, and then designated it as strain YY5A.

This invention thus provides new recombinant yeast strains expressing xylose reductase, xylose dehydrogenase, xylulokinase and transaldolase, and can rapidly ferment xylose to ethanol from synthetic medium and lignocellulosic raw materials.

BRIEF DESCRIPTION OF THE DRAWINGS

A detailed description of further features and advantages of the present invention is given below so that a person skilled in the art can understand and implement the technical contents of the present invention and readily comprehend the objectives, features, and advantages thereof by reviewing the disclosure of the present specification and the appended claims in conjunction with the accompanying drawings, in which:

DETAILED DESCRIPTION OF THE PREFERRED EMBODIMENTS

Genetically engineered *Saccharomyces cerevisiae* has been developed to improve the capacity for converting xylose into ethanol because of the potential applicability for the cellulosic ethanol industry. Thus, this invention is aimed at providing a method for enhancing the ethanol yield and sugar consumption rate from xylose for recombinant *S. cerevisiae*.

A number of efforts have focused on the initial xylose metabolic pathway in *Saccharomyces cerevisiae* in view of its critical role in the capability of xylose utilization. Initial xylose metabolic pathways include XR-XDH and XI systems. To make gene acquirement easy, XR-XDH system is used in this invention. Xylose metabolic enzymes of XR-XDH system in the initial xylose metabolism include xylose reductase (XR), xylitol dehydrogenase (XDH) and xylulokinase (XK). Several reports have shown that higher activity of XR increases the xylose consumption rate of *S. cerevisiae* during the fermentation, but insufficient XDH activity leads to the by-product accumulation of xylitol. XK is prerequisite, but only fine-tuned overexpression of XK gene is capable of improving the xylose metabolic flux. In addition, excess XK activity could result in rapid depletion of ATP and X5P accumulation, and may result in cell toxicity. Cofactor balance between XR and XDH is also important for reducing the xylitol accumulation and improving the xylose utilization. Numerous studies have indicated that efficient utilization of xylose by recombinant *S. cerevisiae* is directly involved with the specific cofactor usage and the ratio of enzymes activities in xylose metabolic pathway. Therefore, there is not just one rate-limiting step in the xylose metabolic pathway. In order to optimize the XR-XDH system in *S. cerevisiae*, a novel method is described herein.

Figure 3:
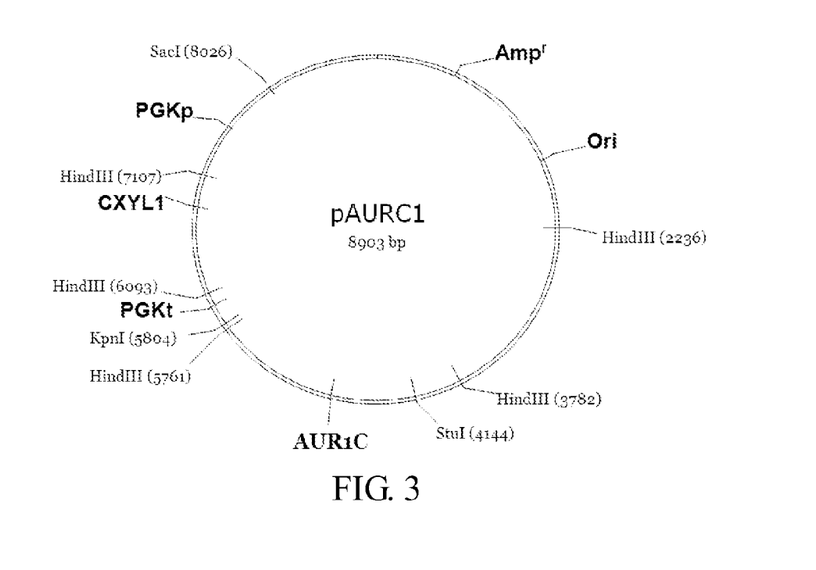
FIG. 3 shows the restriction map of pAURC1 and the genes cloned within.
Figure 4:
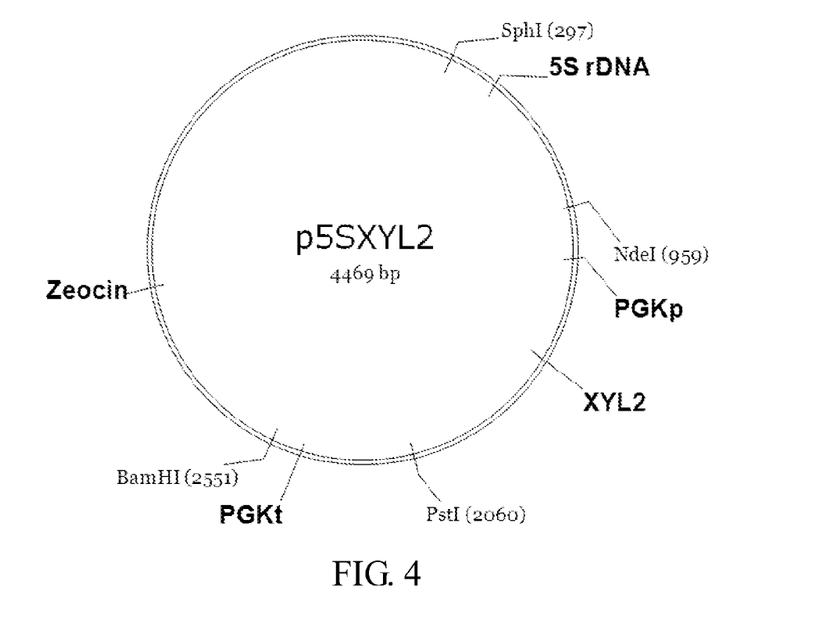
FIG. 4 shows the restriction map of p5S-XYL2 and the genes cloned within.
Figure 5:
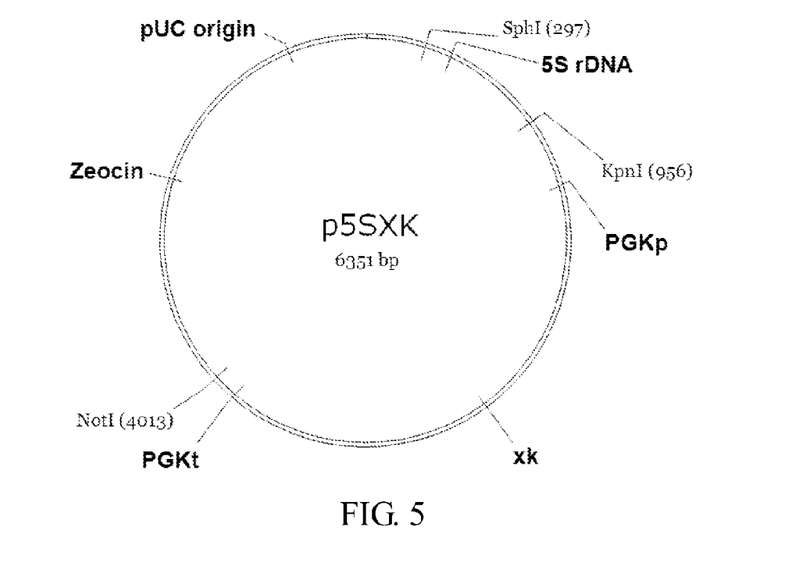
FIG. 5 shows the restriction map of p5S-XK and the genes cloned within.
Figure 6:
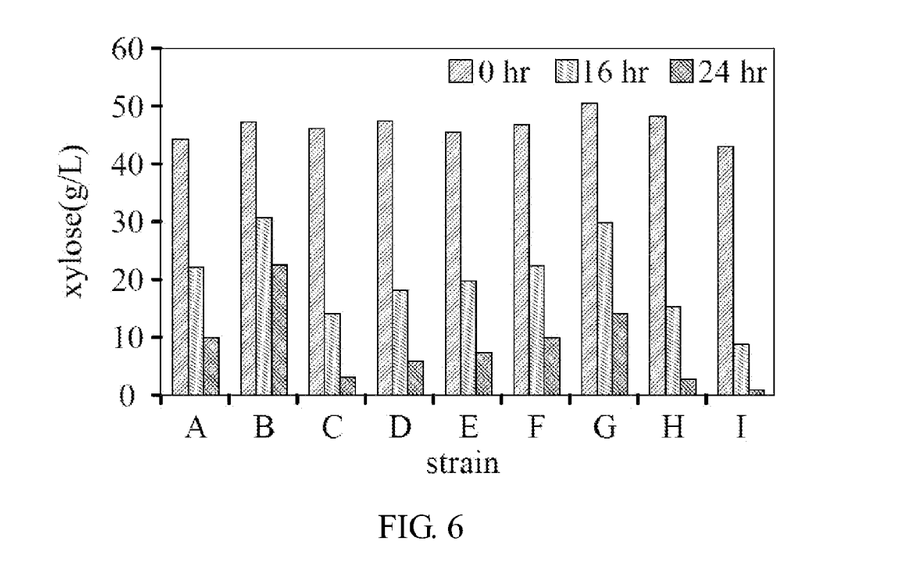
FIG. 6 shows the consumption of xylose by recombinant yeasts during 24 hr fermentation in YPX synthetic medium.
Figure 7:
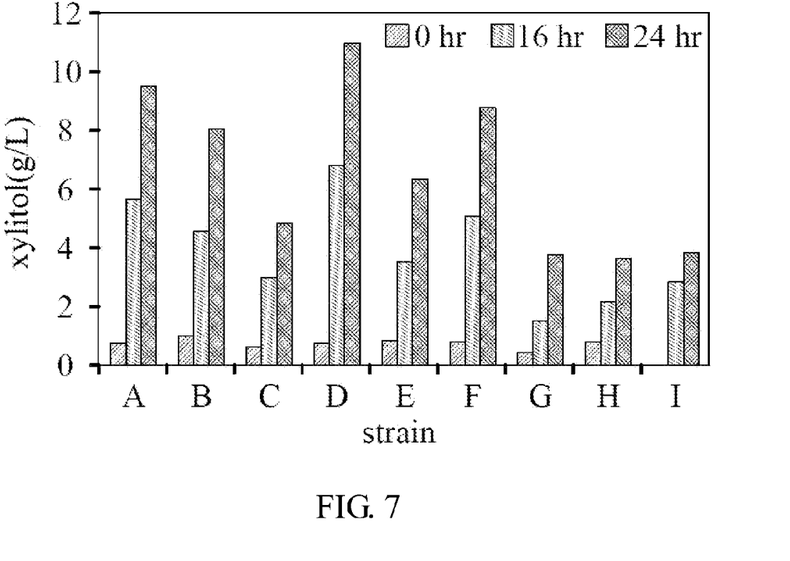
FIG. 7 shows the accumulation of xylitol by recombinant yeasts during 24 hr fermentation in YPX synthetic medium.
Figure 8:
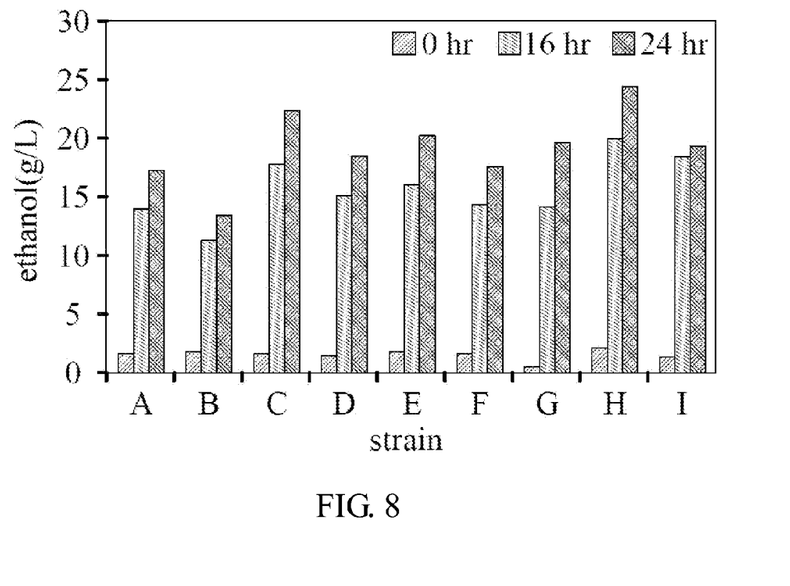
FIG. 8 shows the accumulation of ethanol by recombinant yeasts during 24 hr fermentation in YPX synthetic medium.
Figure 9:
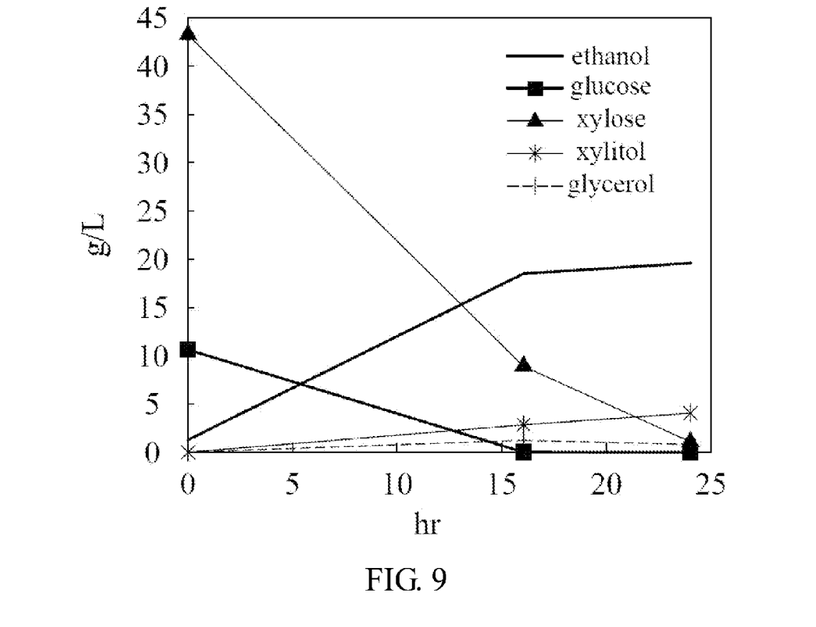
FIG. 9 is a time-dependent batch fermentation profile of the recombinant yeast YY5A in YPX synthetic medium.
Figure 10:
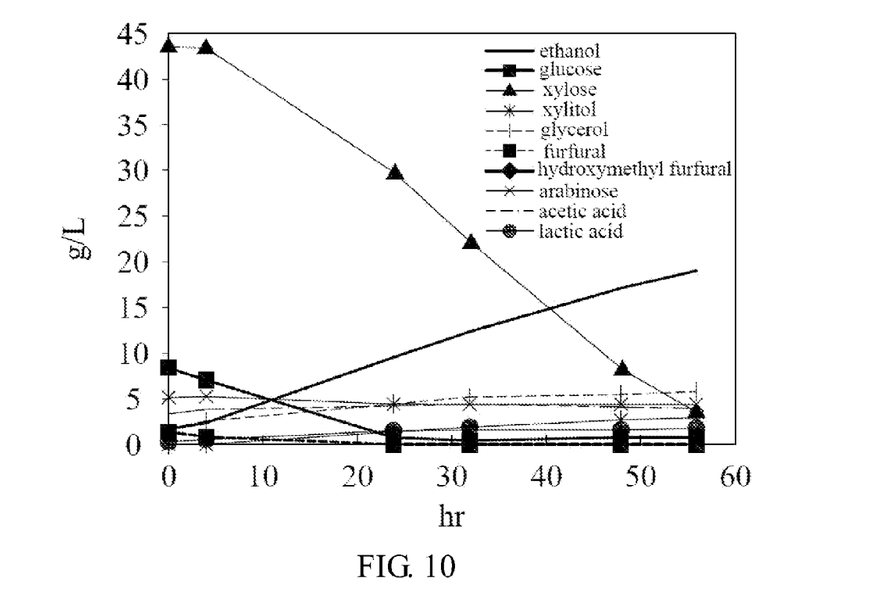
FIG. 10 is a time-dependent batch fermentation profile of the recombinant yeast YY5A in lignocellulosic hydrolysate.

The *Saccharomyces cerevisiae* strain YY2KL with a lower capability of xylose utilization was used as a parental host for genetic engineering. The genotype of YY2KL contains xylose metabolic genes encoding xylose reductase (XR) from *Candida guilliermondii*, xylitol dehydrogenase (XDH) from *Pichia stipitis*, endogenous xylulokinase (XKS1) and transaldolase (TAL) from *Pichia stipitis*. Except TAL gene is under control of the TEF promoter, the others are of PGK promoter, both of TEF and PGK promoters are constitutive promoters. The parental host used for YY2KL was *S. cerevisiae* ATCC20270. In order to increase the xylose consumption rate of YY2KL, the strain was integrated with extra copies of cXR gene by transforming with the chromosomal integration plasmid pAURC1 (FIG. 3). The plasmid pAURC1 derived from pAUR101 (TAKARA Bio.) contained cXR gene under control of PGK promoter and aur1 sequence for integrating the expressing plasmids into the chromosome of the strain. Transformed cells were selected on YPD medium with 0.5 mg/L of Aureobasidine A (Takara Bio). The transformants appeared within 3 days at 30° C. The newly recombinant yeast strain was selected and named YYA1. To verify the increased capability of xylose utilization of YYA1, xylose fermentation of the parental strain YY2KL and the genetically modified strain YYA1 was evaluated in 250 ml flask containing 50 ml YPX synthetic medium (1% yeast extracts, 2% peptone, 2% xylose). The result indicates that the xylose consumption rate of YYA1 is increased compared to the parental strain, but the xylitol yield is also increased. Thus, higher activity of XR in *S. cerevisiae* could increase the xylose consumption rate, but insufficient XDH may result in xylitol accumulation. To reduce the accumulation of the xylitol, the strain was integrated with extra copies of XDH and XK genes by transforming with the chromosomal integration plasmids p5SXDH and p5SXK. The plasmids p5SXDH and p5SXK derived from pGAPZαA (Invitrogen) contained XDH and XKS1 genes respectively, both of the genes were under control of PGK promoter. Both of the plasmids also contained the 5S rDNA sequence from *S. cerevisiae* ATCC 20270 for integrating the expressing plasmids into the chromosome of the strain. Transformed cells were selected on YPX medium with 400 mg/L of Zeocin (Invitrogen). The transformants appeared within 3 days at 30° C. 14 well-growth colonies with different fermentation capacities of xylose were selected in YPX medium. To verify the xylose utilization capability of the selected strains, xylose fermentation was further evaluated in a 250 ml flask that contains 50 ml YPX synthetic medium. The results indicate that the xylose consumption rates of the selected strains were increased and the xylitol yields were reduced. Consequently, a recombinant strain with an attractive capacity for xylose fermentation was selected, and then designated it as strain YY5A. The yeast *S. cerevisiae* carries 100-200 copies of the rDNA unit that are randomly repeated on chromosome XII. Because of the expressing plasmids randomly integrating into the sequence sites of 5S rDNA, the recombinant *S. cerevisiae* library was built with different ratios of enzyme activity in XR-XDH-XK metabolic pathway. The recombinant strains with the correct ratios of enzyme activity grew well on YPX medium than others, thus the optimized strain can be further selected from a culture on YPX medium.

Ethanolic fermentation of lignocellulose hydrolysates requires that the organism is capable of fermenting in the presence of inhibitory compounds including weak acids, furaldehydes and phenolics. *Saccharomyces cerevisiae*, which has been the preferred organism for fermentative ethanol production, is also tolerant toward lignocellulose derived metabolic inhibitors. Fermentation by YY5A had also been carried out in non-detoxified rice straw hydrolysate (8.6 g/L glucose, 43.6 g/L xylose, 5.1 g/L arabinose, 1.38 g/L furfural, 1.0 g/L HMF). Although the hydrolysate has a high concentration of furaldehyde inhibitors, the result indicates that YY5A is able to efficiently coferment glucose and xylose of hydrolysate to ethanol simultaneously. Above all, the recombinant yeast YY5A prepared by the method in the present invention could rapidly ferment xylose to ethanol from synthetic medium and lignocellulosic raw materials. Preferred embodiments of the method of the present invention are illustrated by way of the following examples:

Example 1

Construction of the Plasmids pB-PGK-XYL2 and pB-PGK-XYL1

A. Preparation of a Plasmid pB-PGK-XYL2

Recombinant plasmid pB-PGK-XYL2 bearing XYL2 gene from *Pichia stipitis* downstream of the PGK promoter and upstream of ADH1 terminator was constructed. The plasmid was prepared by following the steps of:

Using *P. stipitis* chromosome as a template, the XYL2 gene was amplified with primers, Y0811: 5'-TTCACAAGCT-TCATATGACTGCTAACCCTTCCTTG-3' and Y0812: 5'-AAGCGCTGCAGTTACTCAGGGCCGTCAATGAG-3'. HindIII/PstI digested fragment XYL2 was cloned into HindIII/PstI digested plasmid pBluescriptSKII (Stratagene). The resultant recombinant plasmid was pBlue-XYL2.

Using plasmid pAD-GAL4-2.1 (Stratagene) as a template, the DNA fragment comprising a ADH1 promoter and terminator was amplified with primers, Y0801: 5'-AATTAGGGC-CCTCGCGTTGCATTTTTGTTC-3' and Y0802: 5'-AGAGCGAGCTCATGCTATACCTGAGAAAGC-3'. ApaI/SacI digested fragment comprising a ADH1 promoter and terminator was cloned into ApaI/SacI digested plasmid pBluescriptSKII (Stratagene). The resultant recombinant plasmid was pB-ADH-GAL4AD.

Using plasmid pB-ADH-GAL4AD as a template, creating a NdeI restriction site with primers, Y0803: 5'-CAAT-CAACTCCAAGCTTTGCACATATG-GATAAAGCGGAATTAATTC-3' and Y0804: 5'-GAAT-TAATTCCGCTTTATCCATATGTGCAAAGCTTGGAGT-TGATTC-3'. The resultant recombinant plasmid was pB-ADH-GAL4ADN.

Using a plasmid pGG119 (Rinji Akada, Isao Hirosawa, Miho Kawahata, Hisahi Hoshida and Yoshinori Nishizawa, 2002, "Sets of integrating plasmids and gene disruption cassettes containing improved counter-selection markers designed for repeated use in budding yeast," *Yeast*, 19:393-402) as a template, the DNA fragment comprising a PGK promoter was amplified with primers, Y0805: 5'-CCGAAC-CCGGGCCCGAGGAGCTTGGAAAGATGC-3' and Y0806: 5'-ACACTCATATGTTCCGATCTTTTGGTTT-TATATTTG-3'. ApaI/NdeI digested fragment comprising a PGK promoter was cloned into ApaI/NdeI digested plasmid pB-ADH-GAL4ADN. The resultant recombinant plasmid was pB-PGK-GAL4ADN.

Figure 1:
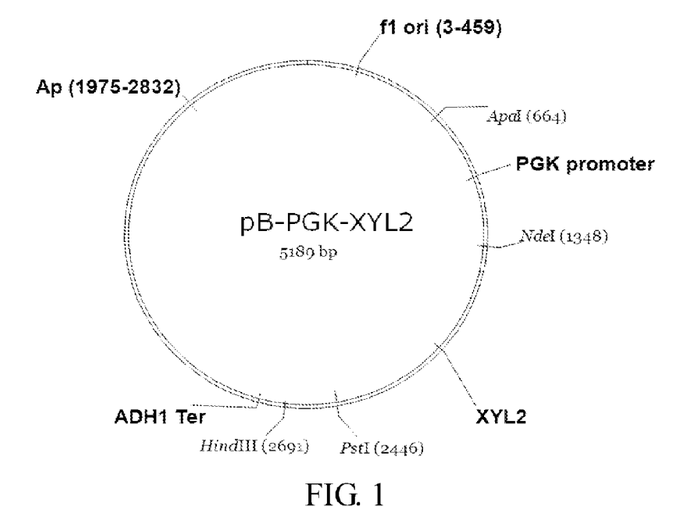
FIG. 1 shows the restriction map of pB-PGK-XYL2 and the genes cloned within.

Finally, NdeI/PstI digested fragment comprising XYL2 gene was cloned into NdeI/PstI digested plasmid pB-ADH-GAL4ADN. The resultant recombinant plasmid was pB-PGK-XYL2 (see FIG. 1).

B. Preparation of a Plasmid pB-PGK-CXYL1

Recombinant plasmid pB-PGK-CXYL1 bearing CXYL1 gene from *Candida guilliermondii* downstream of the PGK promoter and upstream of ADH1 terminator was constructed. The plasmid was prepared by following the steps of:

Using *C. guilliermondii* chromosome as a template, the CXYL1 gene was amplified with primers, Y0903: 5'-GCCG-CATATGTCTATTACTTTGAACTCAG-3' and Y0904: 5'-CGCGGAATTCCATGGTTACACAAAAGT-TGGAATCTTG-3'. HindIII/PstI digested fragment XYL2 was cloned into HindIII/PstI digested plasmid pBluescriptSKII (Stratagene). The resultant recombinant plasmid was pBlue-CXYL1.

Figure 2:
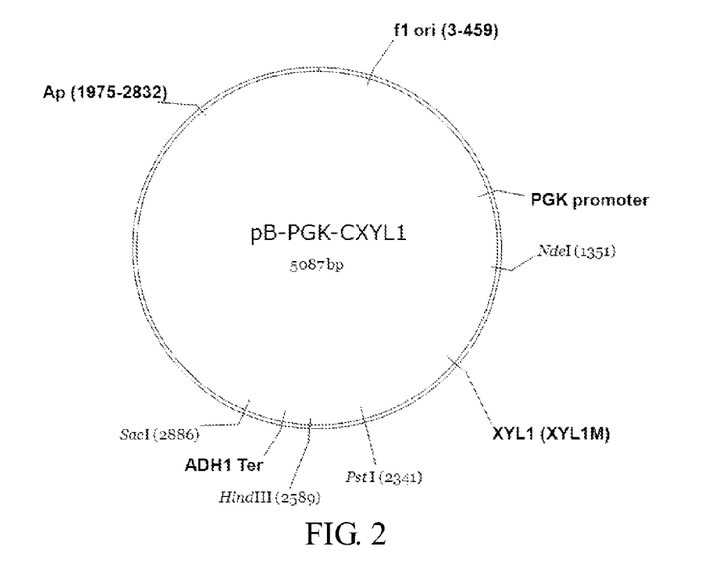
FIG. 2 shows the restriction map of pB-PGK-CXYL1 and the genes cloned within.

Finally, NdeI/EcoRI digested fragment comprising CXYL1 gene was cloned into NdeI/EcoRI digested plasmid pB-ADH-GAL4ADN. The resultant recombinant plasmid was pB-PGK-CXYL1 (see FIG. 2).

Construction of the Integrating Plasmids pAURC1, p5SXDH and p5SXK

Recombinant plasmid pAURC1 bearing CXYL1 gene from *Candida guilliermondii* downstream of the PGK promoter and upstream of ADH1 terminator was constructed on the basis of pAUR101 shuttle vector (Takara Bio, Kyoto). The sequence of PGK-CXYL1-ADH1 was amplified from pB-PGK-CXYL1 plasmid with primers, PGKKpnIfw: 5'-GG-TACCGAGGAGCTTGGAAAGATGCC-3' and ADH1KpnI/SacIrv: 5'-GGTACCCTGGAGCTCATG CTATACCTGAG-3'. KpnI/SacI digested fragment PGK-CXYL1-ADH1 was cloned into KpnI/SacI digested pAUR101 plasmid. The resultant plasmid was pAURC1. Recombinant plasmids p5SXYL2 and p5SXK bearing 5S rDNA from *Saccharomyces cerevisiae* and coding sequences of XDH and XK from *Pichia stipitis* respectively were constructed on the basis of the plasmid pGAPZαA (Invitrogen). The sequence of 5s rDNA was amplified from the genomic DNA of *S. cerevisiae* by using the primers: 5SrDNA-F: 5'-AGATCTGTCCCTC-CAAATGTAAAATGG-3' and 5SrDNA-R: 5'-GGTACCG-TAGAAGAGAGGGAAATGGAG-3'. BglII/KpnI digested fragment 5S rDNA was cloned into the BglII/KpnI digested plasmid pGAPZαA. The resultant plasmid was pGAP5S. The sequence of PGK-XYL2-ADH1 was amplified from the plasmids pB-PGK-XYL2 by using the primers: PGKNotIfw-F: 5'-GCGGCCGC GAGGAGCTTGGAAAGATGCC-3' and ADH1BamHIrv-R: 5'-GGATCCCTGGAGCTCATGC-TATACCTGAG-3'. The NotI/BamHI digested PGK-XYL2-ADH1 fragment was cloned into the NotI/BamHI digested plasmid pGAP5S. The resultant plasmid was p5SXYL2. The genomic region of *Pichia stipitis* encompassing the entire coding sequence of XK was amplified with primers, XK-F: 5'-CATATGATGACCACTACCCCATTTG-3' and XK-R: 5'-CTG CAGTTAGTGTTTCAATTCACTTTCC-3'. The NdeI/PstI digested XK amplified DNA fragments were cloned into the NdeI/PstI digested plasmid p5SXYL2 between the PGK promoter and ADH1 terminator. The resultant plasmid was p5SXK.

Example 2

Transformation

Yeast transformation of plasmids pAURC1, p5SXK, p5SXYL2 was carried out by the electroporation method.

YY2KL was transformed with pAURC1 to become a new transformant named YYA1. YY5A was derived from YYA1 which was transformed with p5SXK and p5SXYL2 simultaneously in a 1:2 mole ratio, and then selected in YPX medium with Zeocin (Invitrogen). For electroporation, pAUR101 was linearized with StuI, p5SXK and p5SXYL2 were linearized with SphI. Culture flasks (250 ml) containing 50 ml YPD medium were inoculated with 1 ml of the overnight inoculum culture and grown for approximately 4-5 hours at 30° C. with shaking to attain an absorbance value of 3 units at 600 nm. Cells were harvested in a clinical centrifuge (4000 rpm) and the pellets resuspended with Lithium Acetate buffer (8 ml sterile water, 1 ml Lithium Acetate, 1 ml 10×TE buffer). Then the resuspended pellets were incubated at 30° C. for 45 min. After incubation, brought the volume to 50 ml with sterile water and washed twice. After washing twice, resuspended the pellets with 0.1 ml 1 M sorbitol that is competent cells. Mixed 40 µl competent cells with 1 µg linearized plasmid. 45 µl mixed sample was subjected to electric shock at 1500 volts and 25 microfarads using a Bio-Rad Gene Pulser Xcell (Richmond, Calif., USA). Following electroporation, cells were immediately plated on selective YPX medium with 400 mg/L of Zeocin (Invitrogen). The transformants appeared within 3 days at 30° C. Well-growth colonies with different fermentation capacities of xylose were selected.

Example 3

Strains and Growing Conditions

*S. cerevisiae* BCRC 20270 and recombinant strain YY2KL, YYA1 and YY5A were the *Saccharomyces* strains used in this study. Yeast strains *S. cerevisiae* and transformants were grown in YPD medium (0.5% yeast extract, 2% peptone, 2% glucose). For selection of yeast transformants on YPD medium, 400 mg/L of Zeocin (Invitrogen) or 0.5 ma of Aureobasidine A (Takara Bio) was added. Cultivation of *S. cerevisiae* was performed at 30° C., 150 rpm.

*E. coli* DH5a [F$^-$ 80d lacZ$\Delta$M15 recA1 end1 gyrA96 thi1hsdR$^{17}$ ($m_k^- r_k^-$) supE44 relA1 deoR$\Delta$(lacZYA-argF) U169] was used for subcloning. For selection of *E. coli* transformants on LB medium (1% tryptone, 0.5% yeast extract, 0.5% NaCl) supplemented with 100 mg/L Ampicillin or 25 ma Zeocin. Cultivation of *E. coli* was performed at 37° C., 150 rpm.

Example 4

Molecular-Biology Techniques

Standard cloning techniques were used as described. Genomic DNA of *Pichia stipitis* and *Saccharomyces cerevisiae* was isolated using the Wizard® Genomic DNA Purification Kit (Promega, Madison, Wis., USA). Restriction endonucleases and DNA ligase (New England Biolabs) were used according to the manufacturer specifications. Plasmid isolation from *E. coli* was performed with the Plasmid Mini kit (Qiagen). PCR-amplification of the fragments of interest was done with ExTaq DNA Polymerase (TAKARA BIO INC.). PCRs were performed in GeneAmp® PCR System 9700 thermocycler (Applied Biosystems). Transformation of the yeast *S. cerevisiae* by electroporation was carried out as described previously.

Example 5

Fermentation

For fermentation studies, the seed cultures were grown aerobically in 50 mL of YPD 250-mL Erlenmeyer flask at 30° C. for 16 hr. For ethanol production, 10 mL of seed cultures was used to inoculate into 50 mL of YPX or YPDX medium in a 250-mL Erlenmeyer flask. An initial CDW of 0.4 g/L was used. All fermentations were performed at 30° C. with mild agitation at 150 rpm.

Ethanol fermentation from xylose by sixteen strains including fourteen selected recombinant strains (pAURC1, p5SXDH, p5SXK), YYA1(pAURC1) and parental strain YY2KL was compared using 20 g/L xylose as the sole carbon source (YPX medium). The results indicate that the parental strain YY2KL and the strain YYA1 consumed 44% and 82% xylose in 24 hours, respectively, whereas the optimized strains were able to consume 88.4%-93.7% xylose. The strain YY5A showed the highest xylose consumption rate (0.78 g/L/h) during the fermentation, and produced ethanol with a yield of 0.3 g/g$_{consumed\ xylose}$, xylitol with a yield of 0.1 g/g$_{consumed\ xylose}$. However, YY5A fermenting in the medium with higher concentration of xylose (45 g/L) showed the xylose consumption rate of 1.77 g/L/h, and produced ethanol with a yield of 0.34 g/g$_{consumed\ xylose}$, xylitol with a yield of 0.02 g/g$_{consumed\ xylose}$.

Fermentation by YY5A has also been carried out in non-detoxified rice straw hydrolysate (8.6 g/L glucose, 43.6 g/L xylose, 5.1 g/L arabinose, 1.38 g/L furfural, 1.0 g/L HMF). YY5A consumed 81% xylose in 48 hours and produced maximum ethanol concentration of 17.1 g/L. The ethanol yield corresponds to 71% of the theoretical yield.

Example 6

Analyses

Concentrations of ethanol, glucose, xylose, xylitol, glycerol, and acetic acid were determined by high-performance liquid chromatography (HPLC; JASCO, Tokyo) equipped with a refractive index detector. The column used for separation was HPX-87H ion-exclusion column (Bio-Rad Laboratories, Hercules, Calif., USA). The HPLC apparatus was operated with 5 mM $H_2SO_4$ at a flow rate of 0.6 ml/min as the mobile phase. Cell growth was monitored by measuring the absorbance at 600 nm using spectrophotometer U-3000 (Hitachi). Cell dry weight was determined thrice by filtering 5 mL of a culture through a pre-weighed hydrophilic polyethersulfone filter (PALL, Life Sciences, Michigan, USA). The average measurements are based on three independent experiments.

What is claimed is:

1. A method for preparing a xylose-utilizing strain, wherein the xylose-utilizing strain is *Saccharomyces cerevisiae* having xylose metabolic genes, such that the xylose-utilizing strain not only uses xylose as a main growth carbon source but also ferments glucose and xylose, wherein two expressing plasmids p5SXK and p5SXYL2 having xylose metabolic genes XK and XYL2 are transferred to the xylose-utilizing strain, wherein the genes transferred to the xylose-utilizing strain are further integrated into a chromosome of the xylose-utilizing strain, wherein the xylose-utilizing stain is deposited, with deposition number BCRC 920072, at Food Industry Research and Development Institute Taiwan.

2. The method of claim 1, wherein the xylose fermented by the xylose-utilizing *Saccharomyces cerevisiae* strain is sourced from non-detoxified lignocellulosic raw materials.

3. The method of claim 1, wherein the xylose-utilizing *Saccharomyces cerevisiae* strain coferments glucose and xylose to ethanol.

4. The method of claim 1, wherein the glucose and xylose are sourced from non-detoxified lignocellulosic raw materials.

* * * * *